United States Patent
Singh et al.

(10) Patent No.: US 7,482,361 B2
(45) Date of Patent: Jan. 27, 2009

(54) CRYSTALLINE FORM FOR QUINAPRIL HYDROCHLORIDE AND PROCESS FOR PREPARING THE SAME

(75) Inventors: Girij Pal Singh, Pune (IN); Govind Singh Rawat, Pune (IN); Vilas Nathu Dhake, Pune (IN); Sagar Purshottam Nehate, Pune (IN)

(73) Assignee: Lupin Limited, Maharashtra (IN)

( * ) Notice: Subject to any disclaimer, the term of this patent is extended or adjusted under 35 U.S.C. 154(b) by 596 days.

(21) Appl. No.: 10/538,858

(22) PCT Filed: Dec. 16, 2002

(86) PCT No.: PCT/IN02/00235

§ 371 (c)(1),
(2), (4) Date: Jun. 14, 2005

(87) PCT Pub. No.: WO2004/054980

PCT Pub. Date: Jul. 1, 2004

(65) Prior Publication Data

US 2006/0058347 A1    Mar. 16, 2006

(51) Int. Cl.
C07D 217/06 (2006.01)
A61K 31/47 (2006.01)

(52) U.S. Cl. .................. 514/310; 546/146; 546/147

(58) Field of Classification Search .................. None
See application file for complete search history.

(56) References Cited

U.S. PATENT DOCUMENTS

| 4,344,949 A | 8/1982 | Hoefle et al. |
| 4,761,479 A | 8/1988 | Goel et al. |

FOREIGN PATENT DOCUMENTS

| CA | 2 293 705 | 3/1998 |
| EP | 0 065 301 | 11/1982 |
| EP | 0 285 992 | 10/1988 |
| EP | 0 992 495 | 4/2000 |
| GB | 2 095 252 | 9/1982 |

OTHER PUBLICATIONS

US Department of Health and Human Services, FDA, Guidance for the Industry, Q3C-Tables and List, pp. 1-10, Nov. 2003.*

* cited by examiner

*Primary Examiner*—Zinna N Davis
(74) *Attorney, Agent, or Firm*—Hamre, Schumann, Mueller & Larson, P.C.

(57) ABSTRACT

A novel crystalline form of quinapril hydrochloride of formula (I)

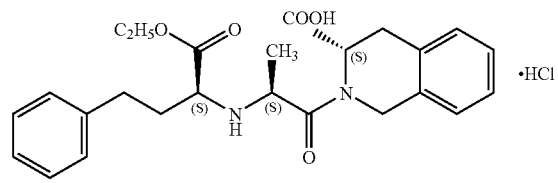

An amorphous form of quinapril hydrochloride substantially free of impurities, specially diketopiperazine compound, and conforming to pharmacopoeial specifications formed from the said novel crystalline form of quinapril hydrochloride of formula (I). The crystalline quinapril hydrochloride is in the form nitroalkane solvate in which the nitroalkane is nitromethane, nitroethane and nitropropanae. Each such nitroalkane solvate having particular characteristic X-ray diffraction patterns. A process for preparation of amorphous form of quinapril hydrochloride, substantially free of impurities, specially diketopiperazine compound, and conforming to pharmacopoeial specifications, using the novel crystalline quinapril hydrochloride as an intermediate. The process involves obtaining free base compound of formula (V) by adjusting the pH of a solution of the benzyl ester maleate salt of quinapril of formula (V) between 7.5-8.5 in a mixture of water and an organic solvent; catalytic hydrogenation of this compound (V) in an alcoholic solvent in the presence of concentrated hydrochloric acid or hydrogen chloride dissolved in an alcoholic solvent and in the presence of catalytic amounts of Pd/C to obtain a residue containing formula (I); crystallization of the said residue by evaporating the alcoholic solvent from a nitroalkane solvent to give crystalline quinapril hydrochloride, associated with a solvate of the nitroalkane solvent, and drying the crystalline quinapril hydrochloride nitroalkane solvate at a temperature between 40° C. and 45° C. under vacuum to give amorphous quinapril hydrochloride of formula (I).

29 Claims, 6 Drawing Sheets

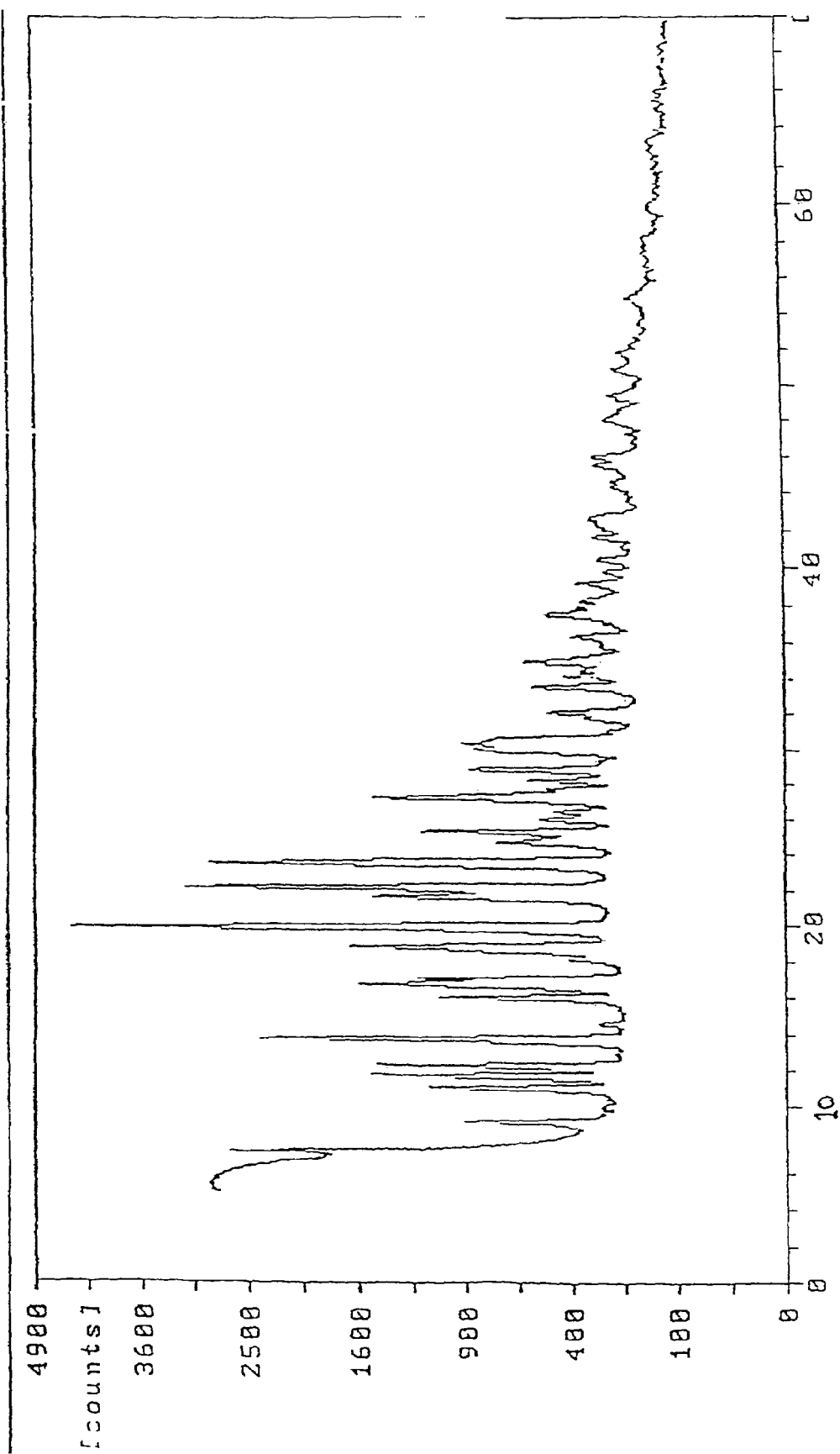
Fig-1a: X-Ray (powder) diffraction pattern of quinapril hydrochloride crystallized from nitromethane.

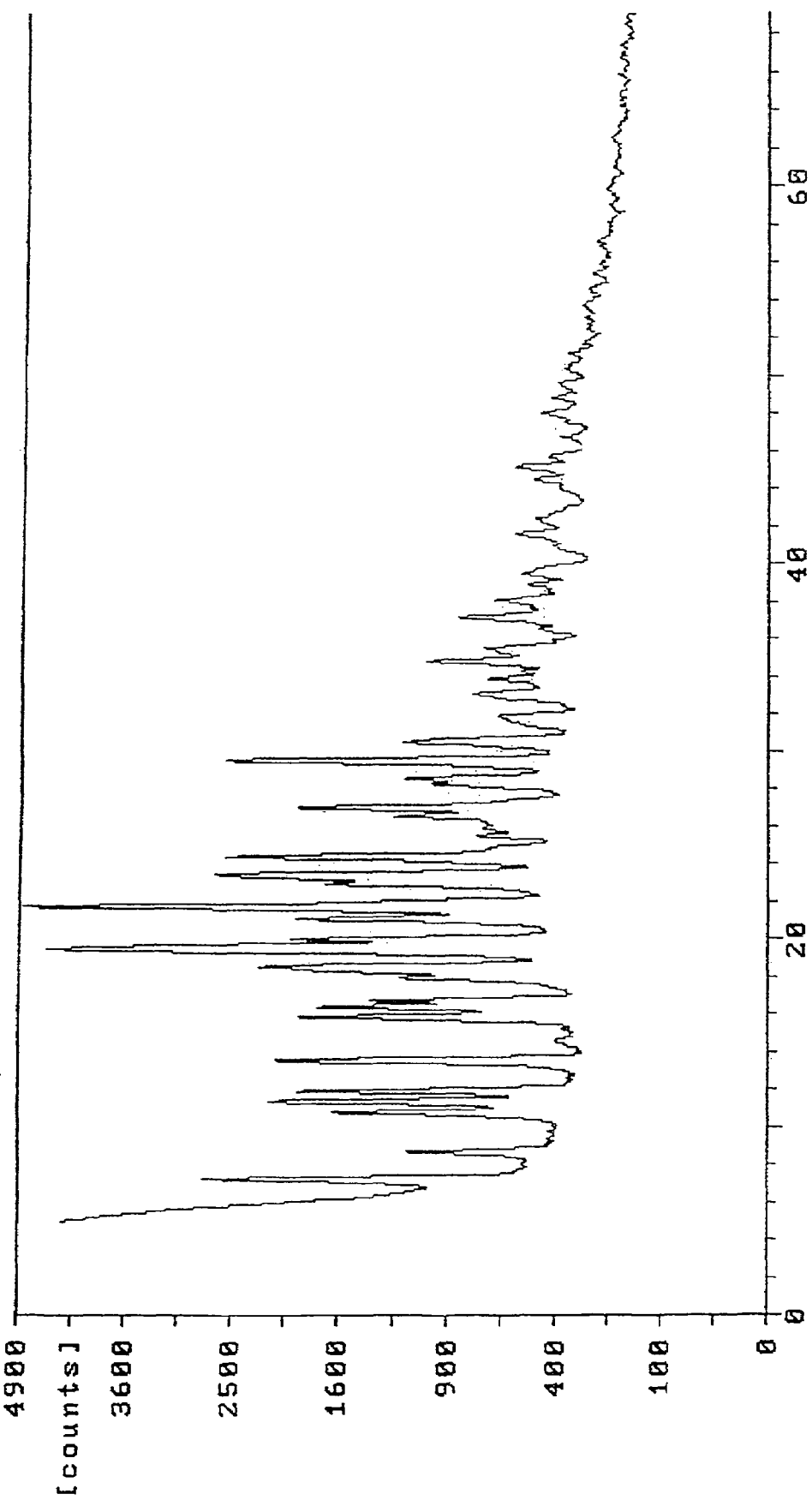
Fig-1b: X-Ray (powder) diffraction pattern of quinapril hydrochloride crystallized from nitroethane.

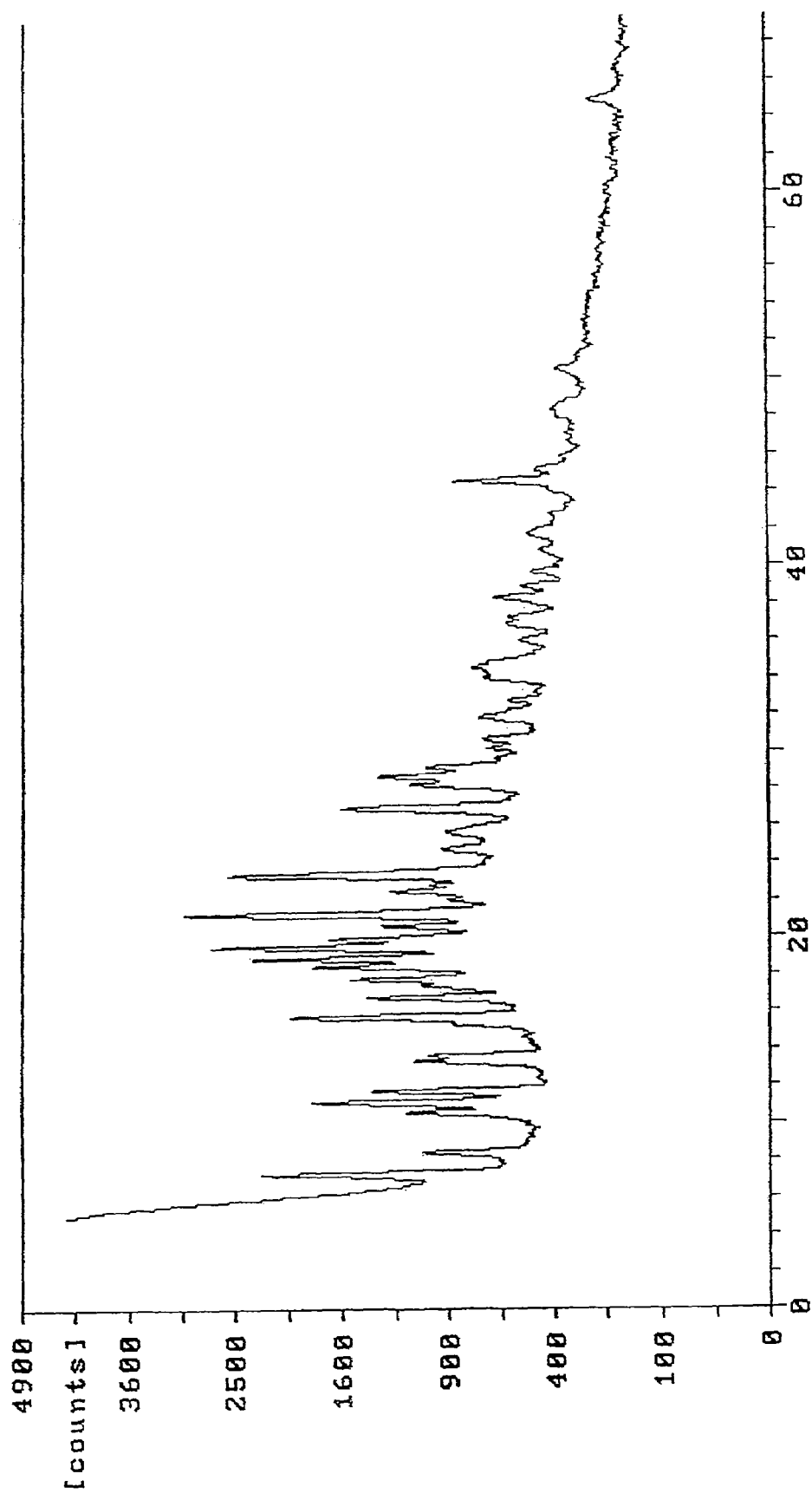
Fig-1c: X-Ray (powder) diffraction pattern of quinapril hydrochloride crystallized from nitropropane.

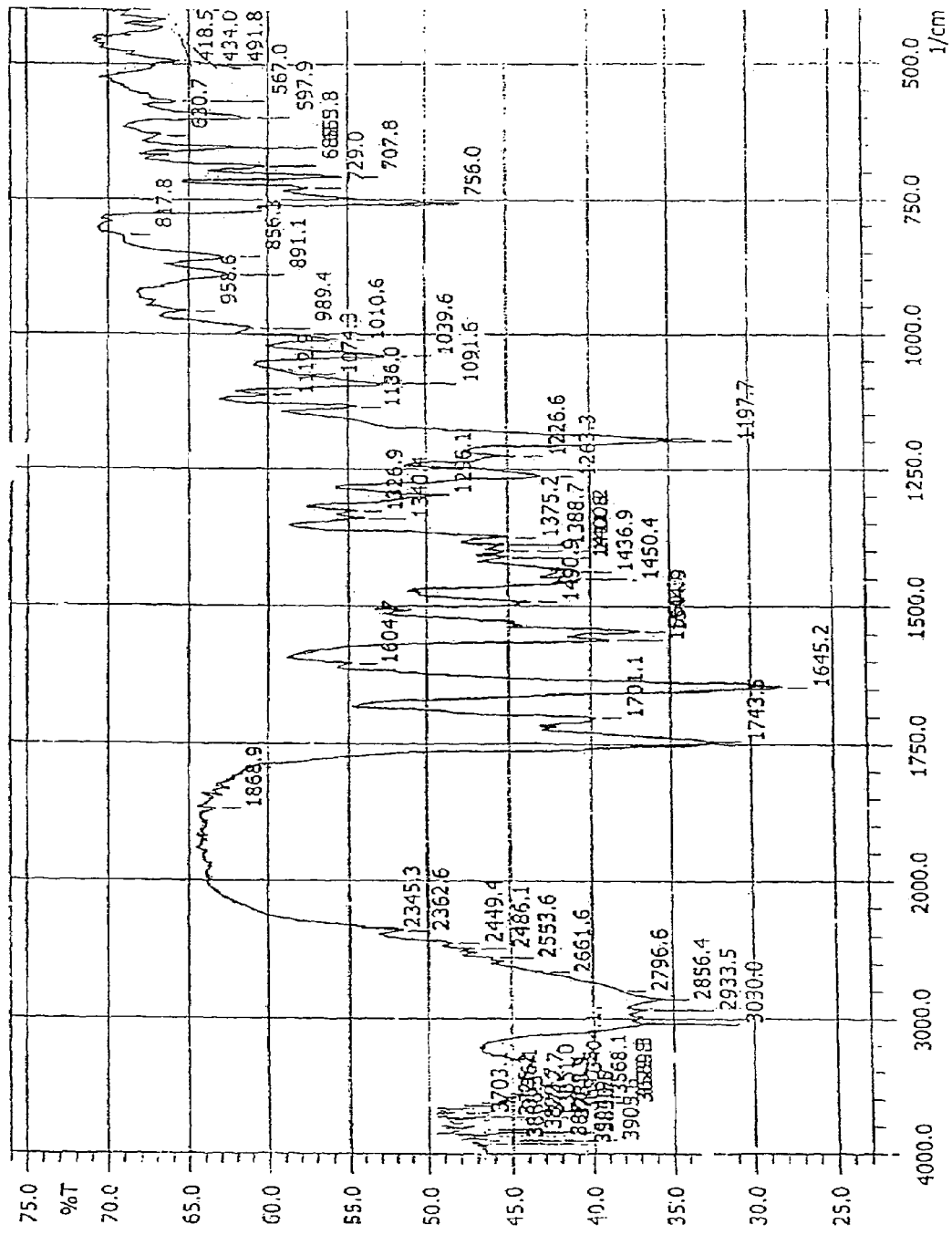

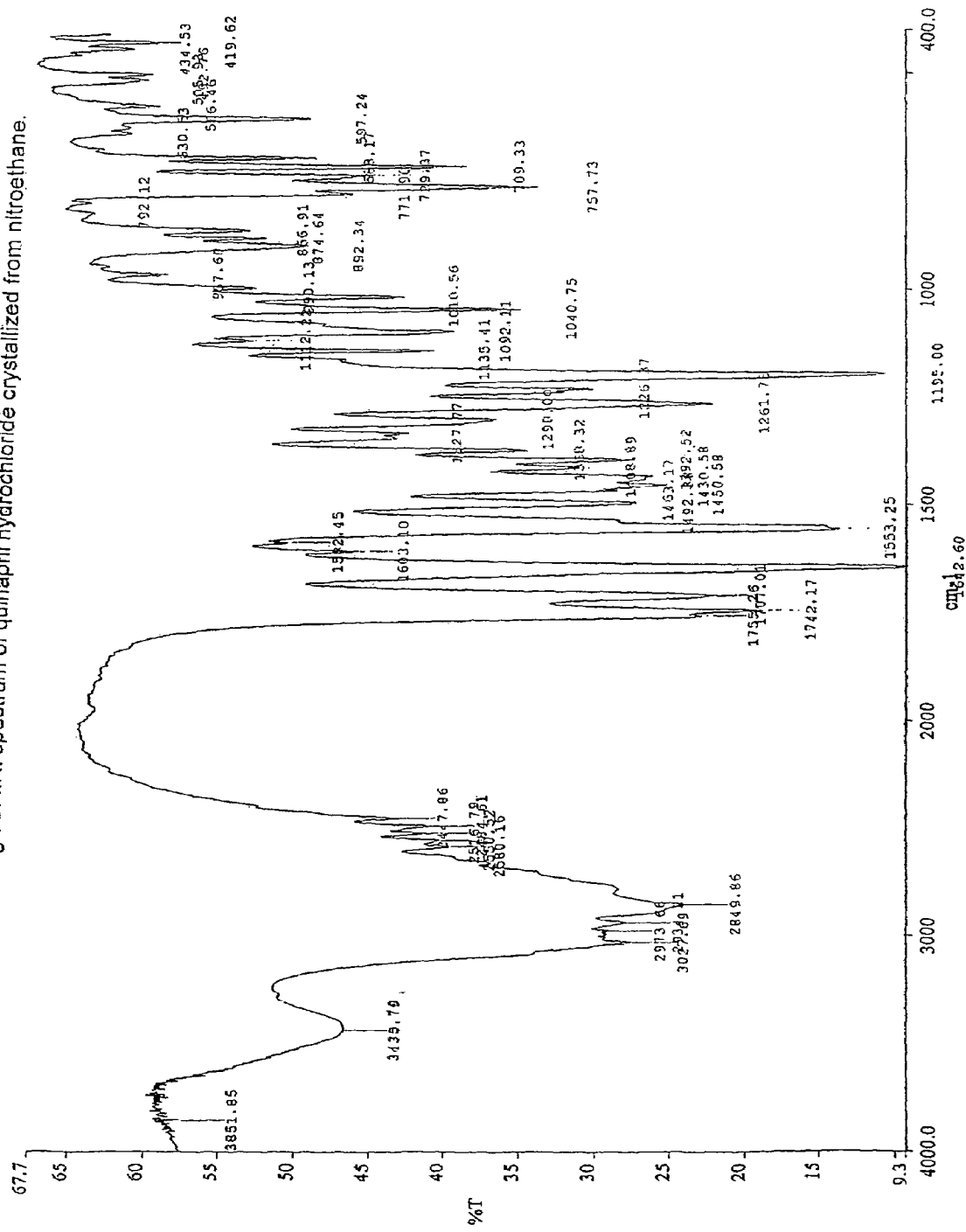
Fig-IIb: I.R. spectrum of quinapril hydrochloride crystallized from nitroethane.

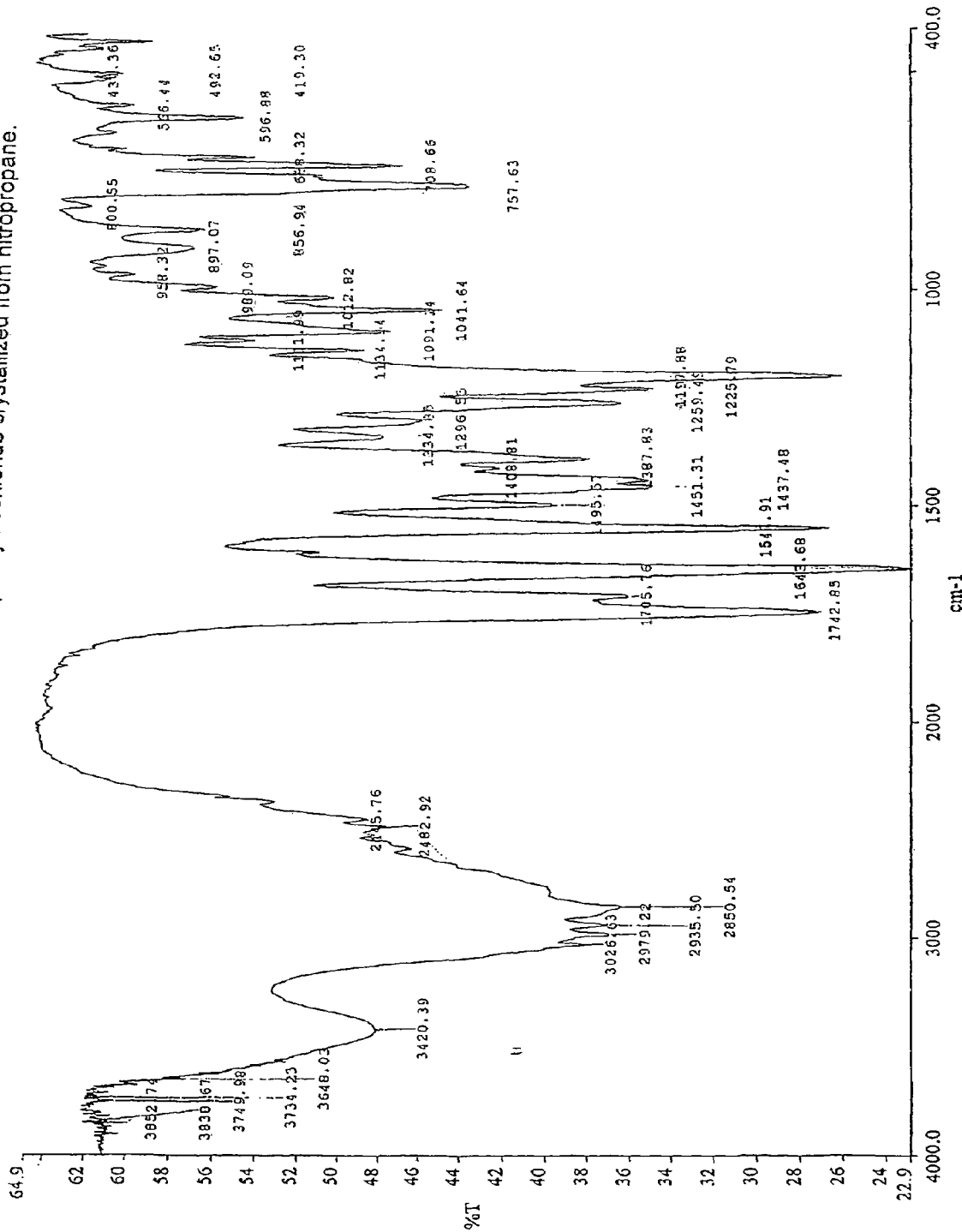

CRYSTALLINE FORM FOR QUINAPRIL HYDROCHLORIDE AND PROCESS FOR PREPARING THE SAME

This application is a 371 of PCT/IN02/00235 filed Dec. 16, 2002.

FIELD OF THE INVENTION

The present invention relates to a novel crystalline form of quinapril hydrochloride of formula (I) and a process for its preparation thereof. The present invention further relates to the preparation of amorphous form of quinapril hydrochloride, of high purity and conforming to pharmacopoeial specifications, by the use of the novel crystalline quinapril hydrochloride of formula (I) as an intermediate.

BACKGROUND OF THE INVENTION

The chemical species, (3S)-2-[(2S)-2-[[(1S)-1-(Ethoxy-carbonyl)-3-phenylpropyl]amino]-1-oxopropyl]-1,2,3,4tet-rahydro-3-isoquinolinecarboxylic acid is known generically as quinapril. Its pharmaceutically acceptable salts, specially the hydrochloride salt is represented by formula (I).

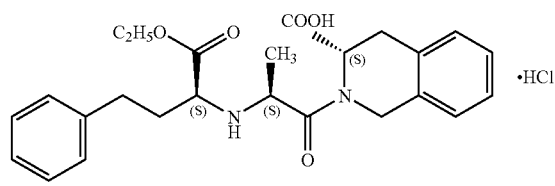

Quinapril hydrochloride (I) and its pharmaceutically acceptable salts are active as angiotensin converting enzyme (ACE) inhibitors and thus are commercially valuable antihypertensive agents.

U.S. Pat. No. 4,344,949 (Hoefle et. al.) inter alia describes a process for the preparation of quinapril hydrochloride comprising reaction of ethyl ester of (S,S)-α-[(1-carboxyethyl) aminio] phenylbutanoic acid with the benzyl or t-butyl ester of (S)-1,2,3,4-tetrahydro-3-isoquinoline carboxylic acid in the presence of 1-hydroxy benzotriazole, employing standard peptide bond forming methods.

The benzyl or t-butyl ester group of quinapril thus obtained is removed by catalytic hydrogenation or by treatment with trifluoroacetic acid. Quinapril hydrochloride is isolated either by solvent precipitation with diethyl ether or by lyophilisation of the aqueous solution.

The above method is summarised in scheme (I).

Scheme I:
Synthesis of quinapril hydrochloride as disclosed in U.S. Pat. No. 4,344,949

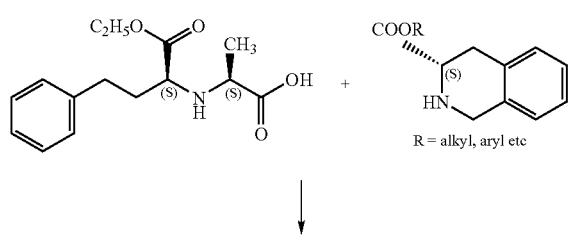

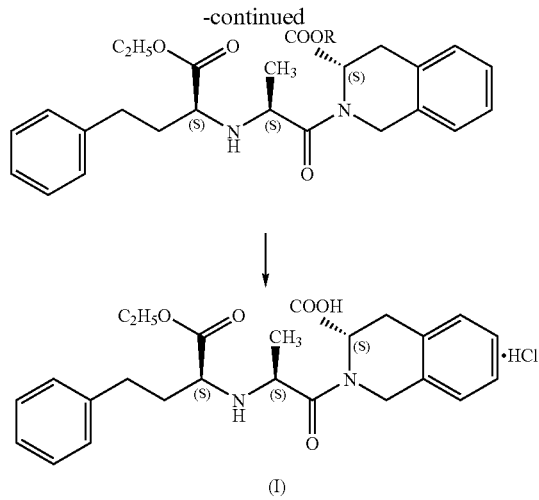

Other methods for preparation of quinapril hydrochloride are disclosed by Barton et. al. in GB Patent No. 2,095,252, by Patchett et. al. in EP Patent No. 0,065,301 etc.

However, all the reported methods for synthesis of quinapril suffer from a serious drawback in that the product obtained by all the methods is invariably contaminated with varying amounts of an impurity identified as the diketopiperazine derivative of formula (II), leading, most often to product not conforming to pharmacopoeial specifications.

The diketopiperazine impurity is formed either during removal of the carboxylic acid protective group or it could be formed during drying of quinapril hydrochloride.

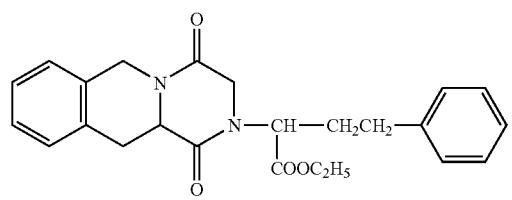

The above impurity once formed is difficult to remove by conventional separation techniques, including fractional crystallization.

Regulatory authorities all over the world are becoming very stringent about the purity of an approved drug or a drug candidate awaiting approval. Especially there is a growing concern about the nature and level of impurities present in such molecules.

Pharmaceutical manufacturers throughout the world, constantly strive to produce drug molecules that go beyond pharmacopoeial specifications i.e. compounds having extra pharmacopoeial specifications.

U.S. Pat. No. 4,761,479 (Goel et. al.) discloses a method wherein quinapril hydrochloride obtained from the reaction mixture is crystallized from a solvent selected from acetonitrile or acetone to give a crystalline form of quinapril hydrochloride possessing a characteristic X-ray (powder) diffraction pattern and high bulk density.

The abovementioned patent also mentions that the crystalline material thus obtained contains equimolar amounts of acetonitrile/acetone as part of the crystal lattice. The patent further mentions that the solvent(s) present in the crystal structure can be removed under vacuum at a temperature of about 50° C. However during this unit operation the crystallinity of the substance is lost due to desolvation during drying, and an amorphous material is obtained which is claimed to be free of impurities, specially the diketopiperazine compound of formula (II).

Even though, the U.S. Pat. No. 4,761,479 discloses the use of acetonitrile and acetone for crystallization, the former is preferred since, unlike acetonitrile, acetone cannot be removed from the crystal lattice, even on prolonged drying.

Canadian Application No. CA 2,293,705 A1 (Llagostera et. al) describes a process for purification of impure quinapril hydrochloride through a two-step process, comprising first crystallisation of the impure material from toluene followed by another crystallization using a class III solvent as categorized by International Conference of Harmonisation (ICH). The patent also mentions that initially a solvate of quinapril hydrochloride with toluene is formed, which is subsequently substituted by a solvate of the class III solvent used for the second crystallisation. This patent like the aforesaid U.S. Pat. No. 4,761,479 also claims that amorphous quinapril hydochioride is obtained on desolvation of the solvate of the material with the class III solvent through drying. Among the class III solvents disclosed, ethyl formate and methyl acetate are the preferred ones.

However, the abovementioned two methods for purification of impure quinapril hydrochloride utilise solvents which have low flash points eg. the flash point of acetonitrile is 2° C., that of methyl acetate is −16° C., whereas that of ethyl formate is −20° C., rendering their use on commercial scale a hazardous proposition. Moreover, the method disclosed in the later patent i. e. Canadian Application No. 2,293,705 A1 involves a two-step purification, which makes the entire operation not only time consuming but costly.

The need, therefore, exists for a method for obtaining quinapril hydrochloride of high purity which addresses the shortcomings associated with the prior art methods.

SUMMARY OF THE INVENTION

According to the principal aspect of present invention there is provided a pure crystalline quinapril hydrochloride of formula I associated with the solvate of the nitroalkane.

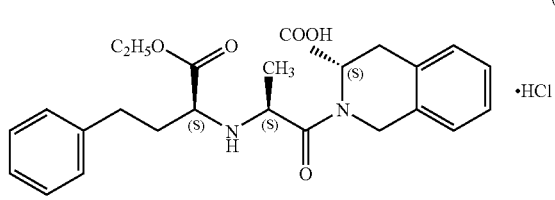

(I)

According to further aspect of the present invention there is provided a novel crystalline nitromethane solvate of quinapril hydrochloride of formula I exhibiting essentially the following X-ray (powder) diffraction properties:

| Spacing 'd' | Relative intensity |
|---|---|
| 16.2471 | 63.5 |
| 13.8426 | 55.5 |

-continued

| Spacing 'd' | Relative intensity |
|---|---|
| 11.9609 | 57.3 |
| 9.6467 | 17.2 |
| 7.9468 | 22.4 |
| 7.5064 | 31.1 |
| 7.1699 | 30.2 |
| 6.4095 | 52.4 |
| 6.0561 | 3.1 |
| 5.5041 | 20.4 |
| 5.2808 | 33.1 |
| 5.1767 | 22.8 |
| 4.8704 | 5.7 |
| 4.6830 | 34.4 |
| 4.4404 | 100 |
| 4.0977 | 30.9 |
| 3.9931 | 69.5 |
| 3.7747 | 62.8 |
| 3.5972 | 12.9 |
| 3.5058 | 22.8 |
| 3.4153 | 8.3 |
| 3.3558 | 7.0 |
| 3.2676 | 30.7 |
| 3.2054 | 7.6 |
| 3.1510 | 9.5 |
| 3.0854 | 16.5 |
| 2.9772 | 14.5 |
| 2.9403 | 17.5 |
| 2.9122 | 12.9 |
| 2.7798 | 7.6 |
| 2.6670 | 9.0 |
| 2.6216 | 6.0 |
| 2.5613 | 10.1 |
| 2.4650 | 5.2 |
| 2.3933 | 7.9 |
| 2.2963 | 4.9 |
| 2.2620 | 2.7 |
| 2.2290 | 3.0 |
| 2.1672 | 3.5 |
| 2.1125 | 3.4 |
| 2.0361 | 2.0 |
| 1.9911 | 3.3 |
| 1.9714 | 3.4 |
| 1.8935 | 2.5 |
| 1.8420 | 2.3 |
| 1.7917 | 2.0 |
| 1.7630 | 1.3 |
| 1.6723 | 1.1 |
| 1.5928 | 0.4 |
| 1.4683 | 0.5 |

According to another aspect of the present invention there is provided a novel crystalline nitroethane solvate of quinapril hydrochloride of formula I exhibiting essentially the following X-ray (powder) diffraction properties:

| Spacing 'd' | Relative intensity |
|---|---|
| 17.4844 | 87.0 |
| 16.0841 | 67.2 |
| 12.0996 | 53.3 |
| 10.0860 | 18.8 |
| 8.1700 | 29.6 |
| 7.7522 | 41.2 |
| 7.3814 | 35.4 |
| 6.5032 | 39.9 |
| 6.0580 | 2.9 |
| 5.5780 | 35.8 |
| 5.3973 | 32.0 |
| 5.2776 | 23.7 |
| 4.9335 | 19.6 |
| 4.8335 | 32.9 |
| 4.7627 | 40.5 |
| 4.5635 | 88.9 |

-continued

| Spacing 'd' | Relative intensity |
|---|---|
| 4.5095 | 69.6 |
| 4.4227 | 36.5 |
| 4.2021 | 36.0 |
| 4.0818 | 100.0 |
| 3.8719 | 30.4 |
| 3.7802 | 48.7 |
| 3.6435 | 49.5 |
| 3.4889 | 10.4 |
| 3.3520 | 20.8 |
| 3.2948 | 36.3 |
| 3.1526 | 15.3 |
| 3.1132 | 19.1 |
| 3.0304 | 49.5 |
| 2.9280 | 19.2 |
| 2.9080 | 14.1 |
| 2.7933 | 7.9 |
| 2.6986 | 10.8 |
| 2.6399 | 9.4 |
| 2.5715 | 16.7 |
| 2.5194 | 9.6 |
| 2.4535 | 4.6 |
| 2.4140 | 12.7 |
| 2.3567 | 8.5 |
| 2.3093 | 5.5 |
| 2.2801 | 6.1 |
| 2.1687 | 6.7 |
| 2.1303 | 4.5 |
| 2.0332 | 5.0 |
| 2.0031 | 6.6 |
| 1.9801 | 3.7 |
| 1.9395 | 2.7 |
| 1.8918 | 4.2 |
| 1.8632 | 3.5 |
| 1.8354 | 3.0 |
| 1.8110 | 2.4 |
| 1.7812 | 2.1 |
| 1.7024 | 1.1 |
| 1.5414 | 0.6 |
| 1.3867 | 0.4 |

According to another aspect of the present invention there is provided a novel crystalline nitropropane solvate of quinapril hydrochloride of formula I exhibiting essentially the following X-ray (powder) diffraction properties

| Spacing 'd' | Relative intensities |
|---|---|
| 17.4327 | 100.0 |
| 15.4378 | 65.5 |
| 12.1079 | 49.5 |
| 10.4492 | 18.2 |
| 8.3626 | 21.3 |
| 7.9183 | 38.9 |
| 7.5253 | 27.5 |
| 6.6268 | 19.6 |
| 6.4583 | 17.2 |
| 5.6238 | 43.2 |
| 5.2713 | 27.8 |
| 5.1011 | 18.3 |
| 4.9816 | 30.7 |
| 4.8049 | 38.7 |
| 4.6878 | 52.0 |
| 4.5427 | 61.4 |
| 4.4480 | 35.3 |
| 4.3008 | 25.3 |
| 4.1690 | 68.6 |
| 4.0279 | 14.7 |
| 3.9483 | 23.9 |
| 3.7993 | 57.5 |
| 3.5871 | 15.5 |
| 3.4582 | 14.8 |
| 3.2960 | 32.0 |
| 3.1558 | 20.6 |
| 3.1053 | 26.1 |
| 3.0548 | 17.9 |
| 2.9559 | 9.2 |
| 2.9066 | 9.9 |
| 2.8044 | 10.6 |
| 2.7274 | 6.5 |
| 2.6357 | 9.4 |
| 2.5910 | 11.1 |
| 2.4880 | 5.3 |
| 2.4365 | 6.4 |
| 2.4053 | 6.0 |
| 2.3446 | 8.4 |
| 2.3084 | 5.2 |
| 2.2682 | 4.1 |
| 2.2075 | 3.0 |
| 2.1667 | 4.1 |
| 2.0297 | 13.7 |
| 2.0023 | 3.5 |
| 1.8765 | 2.2 |
| 1.8019 | 2.6 |
| 1.4337 | 2.2 |
| 1.4005 | 0.4 |

According to a further aspect of the present invention there is provided an amorphous form of quinapril hydrochloride of formula I, in high purity, free of impurites and conforming to pharmacopoeial specifications obtained from the novel crystalline form of quinapril hydrochloride associated with the solvate of the nitroalkane.

Thus according to a still further aspect of the present invention there is provided a simple, industrial method for preparation of quinapril hydrochloride of formula I of high purity.

According to another aspect of the present invention there is provided a simple and industrial method for purification of quinapril hydrochloride of formula I comprisimg crystallisation of impure quinapril hydrochloride from a nitroalkane solvent to give a novel crystalline form of quinapril hydrochloride associated with a solvate of the solvent utilised for crystallisation.

According to further aspect of the present invention there is provided a method for obtaining an amorphous form of quinapril hydrochloride, of high purity, free of impurities and conforming to pharmacopoeial specifications from the novel crystalline form of quinapril hydrochloride associated with the solvate of the nitroalkane solvent.

According to further aspect of the present invention there is provided a method for preparation of amorphous form of quinapril hydrochloride, in high purity, free of impurities and conforming to pharmacopoeial specifications comprising removal of the solvent from the novel crystalline form of quinapril hydrochloride associated with the solvate of the nitroalkane solvent by subjecting the said crystalline form to drying under vacuum.

According to another aspect of the present invention there is provided quinapril hydrochloride of formula I obtained by a simple and industrial method for purification of quinapril hydrochloride comprising crystallisation of impure quinapril hydrochloride from a nitroalkane solvent to give a novel crystalline form of quinapril hydrochloride associated with a solvate of the solvent utilised for crystallisation.

DESCRIPTON OF THE DRAWINGS

FIG. Ia, Ib, and Ic show the X-Ray (powder) diffraction pattern of quinapril hydrochloride crystallized from nitroethane.

FIG. IIa, IIb, and IIc show the I.R. spectrum of quinapril hydrochloride crystallized from nitroethane.

DETAILED DESCRIPTION OF THE INVENTION

According to the present invention, quinapril hydrochloride of formula I

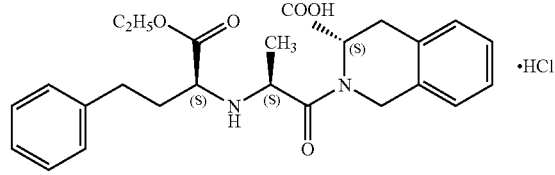

(I)

can be synthesized by two methods, as summarized in Method-I and Method-II.

Method-I:

The first step of Method-I consists of condensation of N-[1(S)-carboethoxy-3-phenylpropyl]-(S)-alanine (III) with the para-toluene sulfonate salt of the benzyl ester of (S)-1,2,3,4-Tetrahydroisoquinoline-3-carboxylic acid (IV) to give the benzyl ester of (S,S,S)-2-{2-{(1-ethoxycarbonyl)-3-phenylpropyl)amino]-1-oxopropyl]-1,2,3,4-tetrahydro-3-isoquinoline carboxylic acid or quinapril benzyl ester which is isolated as the maleic acid salt (V).

Typically, N-[1(S)-carboethoxy-3-phenylpropyl]-(S)-alanine (III) is converted into its acid chloride by reacting with either $PCl_5$ or $PCl_3$ or $SOCl_2$, but preferably with $PCl_5$ in a non-polar or polar solvent, such as those selected from chlorinated hydrocarbons like dichloromethane or 1,2-dichloroethane; aromatic hydrocarbons like toluene, xylene or aliphatic hydrocarbons like hexane, heptane etc. A non-polar solvent is preferred as the acid chloride precipitates out from such solvents and can be easily isolated by filtration.

Method-I: Preparation of quinapril hydrochloride

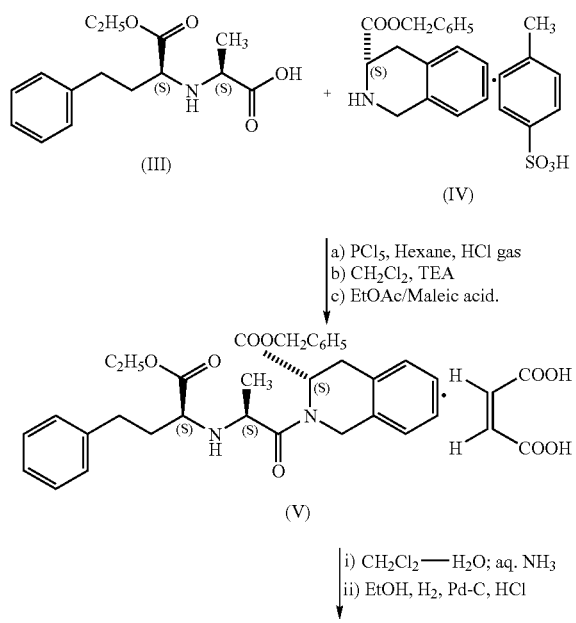

The acid chloride is prepared by treating the acid (III) with $PCl_5$, using hexane as a solvent, the molar ratio of $PCl_5$ used being in the range of 0.9 moles to 1.5 moles, but preferably in the range of 1.0 mole to 1.2 moles.

The reaction temperature employed can be between −5 to +150° C. and for a period of time between 2-5 hrs, but preferably the temperature is in the range of 0-10° C. and reaction time between 3-4 hours.

The acid chloride thus obtained is then condensed with the free base of the benzyl ester of (S)-1,2,3,4-tetrahydroisoquinoline-3-carboxylic acid (IV). The free base is obtained by treatment of the organic or inorganic acid salt of (S)-1,2,3,4-tetrahydroisoquinoline-3-carboxylic acid (IV) with an organic or inorganic base like trialkyl amine, alkali hydroxide etc.

Preparation of compound (V) is then effected in chlorinated solvents like dichloromethane, 1,2-dichloroethane, chloroform etc comprising by addition of the acid chloride of compound (III) to the solution of compound (IV) in the presence of an organic base, such as selected from triethylamine, diethylamine, tertiary butylamine, and dicyclohexylamine at temperatures ranging from −30° C. to 0° C., but preferably at −15 to −20° C. and subsequently raising the temperature in the range of 10-40° C., but preferably 20-30° C. The compound (V) is isolated by washing the organic layer with water and formation of its salt with an organic or an inorganic acid.

In a specific embodiment, a solution of the acid (III) in hexane is reacted with stoichiometric amounts of phosphorous pentachloride at a temperature between 0-10° C., with agitation for 3 hrs. The acid chloride thus formed is isolated by filtration.

A solution of the acid chloride thus obtained is dissolved in dichloromethane and added to the free base of compound (IV). The free base of (IV) is obtained by treating the corresponding p-toluenesulfonate salt with an equimolar amount of organic base, like triethyl amine.

The condensation between the free base of compound (IV) and the acid chloride of compound (III) is carried out in a chlorinated solvent eg. dichloromethane. The acid chloride is added to the free base at −15° C. in the presence of an equimolar amount of an organic base eg. triethyl amine The reaction is then carried forward to completion at room temperature by agitating for a period ranging from 30 to 90 minutes. The reaction mixture is worked up by successively washing the reaction mixture with hydrochloric acid, followed by water and finally with aqueous sodium bicarbonate solution.

Quinapril benzyl ester thus obtained is isolated as its maleate salt by treating the quinapril benzyl ester with maleic acid at room temperature in a alkyl acetate solvent, preferably ethyl acetate.

The second step comprises hydrogenolysis of quinapril benzyl ester maleate salt (V) thus obtained in the presence of Pd/C catalyst and concentrated hydrochloric acid.

The hydrogenolysis of the benzyl ester (V) can be carried out in an alcoholic solvent, such as methanol, ethanol or

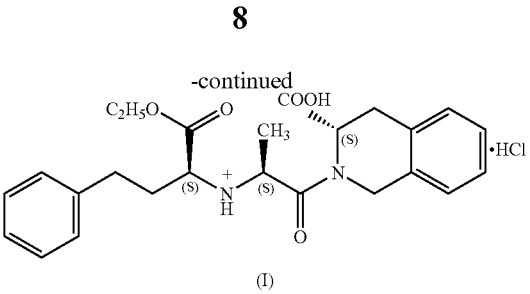

(I)

isopropanol in presence of concentrated hydrochloric acid or a solution of hydrogen chloride in the same alcohol, with hydrogen gas at a pressure ranging between 10-70 psi and at a temperature between 10-40° C.

In a specific embodiment, the hydrogenolysis reaction is carried out on the free base of quinapril benzyl ester (V), which in turn is obtained from the maleate salt (V) by treatment with aqueous ammonia at slightly alkaline pH of 7.5-8.5. Hydrogenolysis is carried out using ethanol as a solvent and in presence of concentrated hydrochloric acid at a pressure ranging between 40-60 psi and room temperature.

The molar ratio between the benzyl ester of quinapril (V) and hydrochloric acid can be equal or greater than the stoichiometric ratio (larger amount of hydrochloric acid in the reaction mixture leads to increase in the diketopiperazine impurity (II), arising due to cyclisation of quinapril hydrochloride under acidic conditions).

The catalyst is removed by filtration and the filtrate evaporated at low temperature, preferably below 30° C. as higher temperature could lead to formation of more amounts of the diketopiperazine impurity (II).

Method-II:

The second method comprises of reacting N [1-(S)-carboethoxy-3-phenylpropyl]-(S)-alanyl carboxyanhydride (VI) with the free base of the benzyl ester of (S)-1,2,3,4-tetrahydroisoquinoline-3-carboxylic acid (IV).

The free base of (IV) is obtained by treating the organic or inorganic acid salt of (S)-1,2,3,4-tetrahydroisoquinoline-3-carboxylic acid (IV) with an organic or inorganic base like trialkyl amine, alkali hydroxide aqueous ammonia etc in a mixture of water and chlorinated solvents like 1,2-dichloroethane, dichloromethane chloroform etc. The pH of the mixture is adjusted between 8.0-9.0 at a temperature between −15 to +15° C., but preferably between 0-10° C. The reaction mixture is then stirred at room temperature, for 15 to 45 minutes, but preferably between 25-35 minutes. The organic layer containing the free base is separated.

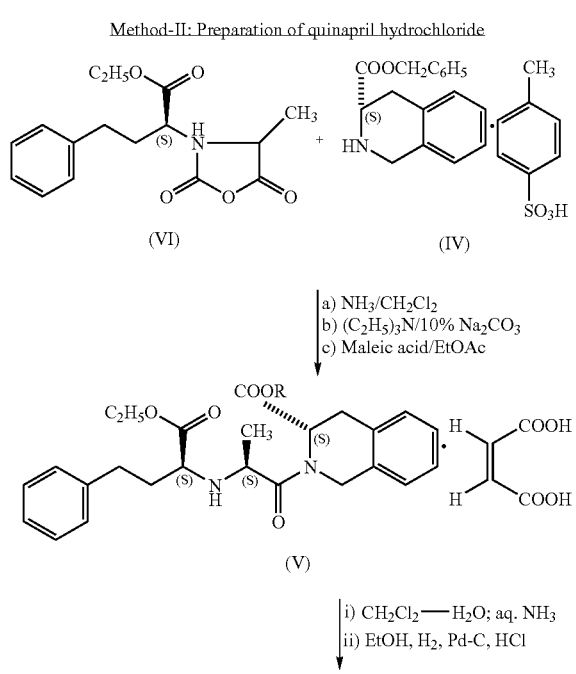

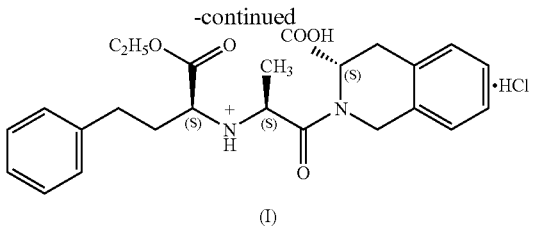

The compound, N [1(S)-carboethoxy-3-phenylpropyl]-(S)-alanyl carboxyanhydride (VI) is dissolved in chlorinated solvents like dichloromethane, 1,2-dichloroethane or chloroform, but preferably in dichloromethane at room temperature. This mixture is then added to the free base of (IV) dissolved in dichloromethane, at a temperature between 20 to 45° C., but preferably at 25 to 35° C. The reaction mixture is agitated for a period between 1 to 5 hours, but preferably between 2 to 4 hours for the reaction to go to completion. A mixture of an aqueous solution of an inorganic base like sodium bicarbonate, sodium carbonate and an organic base like triethyl amine, dicyclohexyl amine etc is added to neutralize the reaction mixture. The organic layer is separated and concentrated and the residue is diluted with an alkyl acetate preferably ethyl acetate. The resultant mixture is stirred at a temperature between 30 to 50° C., but preferably between 35 to 45° C. The product is isolated as a maleate salt as described in method-I.

In a specific embodiment, (S)-1,2,3,4-tetrahydroisoquinoline-3-carboxylic acid (IV), is dissolved in a mixture of water and dichloromethane at 5 to 10° C., and treated with aqueous ammonia solution, at the same temperature. The organic layer is separated and treated with N[1(S)-carboethoxy-3-phenylpropyl]-(S)-alanyl carboxyanhydride (VI), dissolved in dichloromethane at 25-35° C., the resultant mixture is stirred for 2-4 hours, at the same temperature till the reaction goes to completion. The reaction mixture is then neutralized with a mixture of aqueous sodium carbonate and triethyl amine and stirred for 2-4 hours. The organic layer is separated and concentrated, the residue is diluted with ethyl acetate. The mixture is then treated with a mixture of maleic acid dissolved in ethyl acetate to obtain benzyl quinapril ester as the maleate salt as described in method-I.

The benzyl ester quinapril maleate salt is then converted by catalytic hydogenolysis to quinapril hydrochloride, as in method-I.

The residue of quinapril hydrochloride (I) thus obtained is made anhydrous by addition of dry dichloromethane. The resulting mixture is distilled to remove water as an azeotrope. This procedure is repeated until the moisture content of the mixture is less than 1:0%.

The amount of the diketopiperazine impurity (II) present in the quinapril hydrochloride thus obtained varies between 2.0-5.0% by weight of the quinapril hydrochloride.

Purification of the impure quinapril hydrochloride thus obtained is effected by crystallisation from a nitroalkane solvent from which a crystalline form of quinapril hydrochloride falls out. The nitroalkane solvent is selected from nitromethane, nitroethane, and nitropropane. Among these, nitromethane is preferred since it is less costly and readily available.

The nitroalkane solvents like acetonitile belong to Class II solvents as categorised by the International Conference on Harmonisation (ICH). However, unlike acetonitrile these solvents have higher flash point eg. that of nitromethane being 44° C. as compared to 2° C. for acetonitrile, −16° C. for methyl acetate and −20° C. for ethyl formate, rendering them easier and safer to handle during commercial manufacture.

The crystallisation is carried out by addition of the nitroalkane solvent to the anhydrous residue of impure quinapril hydrochloride, obtained as per the method described hereinearlier at room temperature. The mixture is stirred for 10-15 minutes to get a clear solution. The solution is seeded with pure quinapril hydrochloride and then cooled to a temperature ranging between −15 to +15° C., preferably in the range of 0 to +10° C. and agitated at the same temperature for a period of 1-3 hours, preferably 2.0 hrs, to allow the nitroalkane solvate of quinapril hydrochloride to crystallize out. The crystalline solid is filtered out at room temperature.

In a specific embodiment, the impure quinapril hydrochloride is dissolved in nitromethane at room temperature. The amount of nitromethane used can be between 5-10 times by volume, of the weight of the impure material. The solution is seeded with pure quinapril hydrochloride at same temperature and cooled to 5-10° C. The crystalline solvate is allowed to crystallize out at a temperature between 5-10° C. and the crystalline material filtered off at room temperature.

The quinapril hydrochloride to nitroalkane solvate ratio was determined on the basis of $^1$HNMR & HPLC and was found to be having a equimolar ratio.

These novel crystalline solvates quinapril hydrochloride with the nitroalkane solvents possess distinct X-ray (powder) diffraction patterns and these are summarized in Table-I.

TABLE I

X-ray (powder) diffraction pattern of the nitroalkane solvates of quinapril hydrochloride

| Nitromethane | | Nitroethane | | Nitropropane | |
|---|---|---|---|---|---|
| Spacing 'd' | Relative intensity | Spacing 'd' | Relative intensity | Spacing 'd' | Relative intensity |
| 16.247 | 63.5 | 17.4844 | 87.0 | 17.4327 | 100.0 |
| 13.8426 | 55.5 | 16.0841 | 67.2 | 15.4378 | 65.5 |
| 11.9609 | 57.3 | 12.0996 | 53.3 | 12.1079 | 49.5 |
| 9.6467 | 17.2 | 10.0860 | 18.8 | 10.4492 | 18.2 |
| 7.9468 | 22.4 | 8.1700 | 29.6 | 8.3626 | 21.3 |
| 7.5064 | 31.1 | 7.7522 | 41.2 | 7.9183 | 38.9 |
| 7.1699 | 30.2 | 7.3814 | 35.4 | 7.5253 | 27.5 |
| 6.4095 | 52.4 | 6.5032 | 39.9 | 6.6268 | 19.6 |
| 6.0561 | 3.1 | 6.0580 | 2.9 | 6.4583 | 17.2 |
| 5.5041 | 20.4 | 5.5780 | 35.8 | 5.6238 | 43.2 |
| 5.2808 | 33.1 | 5.3973 | 32.0 | 5.2713 | 27.8 |
| 5.1761 | 22.8 | 5.2776 | 23.7 | 5.1011 | 18.3 |
| 4.8704 | 5.7 | 4.9335 | 19.6 | 4.9816 | 30.7 |
| 4.6830 | 34.4 | 4.8335 | 32.9 | 4.8049 | 38.7 |
| 4.4404 | 100 | 4.7627 | 40.5 | 4.6878 | 52.0 |
| 4.0977 | 30.9 | 4.5635 | 88.9 | 4.5427 | 61.4 |
| 3.9931 | 69.5 | 4.5095 | 69.6 | 4.4480 | 35.3 |
| 3.7747 | 62.8 | 4.4227 | 36.5 | 4.3008 | 25.3 |
| 3.5972 | 12.9 | 4.2021 | 36.0 | 4.1690 | 68.6 |
| 3.5058 | 22.8 | 4.0818 | 100.0 | 4.0279 | 14.7 |
| 3.4153 | 8.3 | 3.8719 | 30.4 | 3.9483 | 23.9 |
| 3.3558 | 7.0 | 3.7802 | 48.7 | 3.7993 | 57.5 |
| 3.2676 | 30.7 | 3.6435 | 49.5 | 3.5871 | 15.5 |
| 3.2054 | 7.6 | 3.4889 | 10.4 | 3.4582 | 14.8 |
| 3.1510 | 9.5 | 3.3520 | 20.8 | 3.2960 | 32.0 |
| 3.0854 | 16.5 | 3.2948 | 36.3 | 3.1558 | 20.6 |
| 2.9772 | 14.5 | 3.1526 | 15.3 | 3.1053 | 26.1 |
| 2.9403 | 17.5 | 3.1132 | 19.1 | 3.0548 | 17.9 |
| 2.9122 | 12.9 | 3.0204 | 49.5 | 2.9559 | 9.2 |
| 2.7798 | 7.6 | 2.9280 | 19.2 | 2.9066 | 9.9 |
| 2.6670 | 9.0 | 2.9080 | 14.1 | 2.8044 | 10.6 |
| 2.6216 | 6.0 | 2.7933 | 7.9 | 2.7274 | 6.5 |
| 2.5613 | 10.1 | 2.6986 | 10.8 | 2.6357 | 9.4 |
| 2.4650 | 5.2 | 2.6399 | 9.4 | 2.5910 | 11.1 |
| 2.3933 | 7.9 | 2.5715 | 16.7 | 2.4880 | 5.3 |
| 2.2963 | 4.9 | 2.5194 | 9.6 | 2.4365 | 6.4 |
| 2.2620 | 2.7 | 2.4535 | 4.6 | 2.4053 | 6.0 |

TABLE I-continued

X-ray (powder) diffraction pattern of the nitroalkane solvates of quinapril hydrochloride

| Nitromethane | | Nitroethane | | Nitropropane | |
|---|---|---|---|---|---|
| Spacing 'd' | Relative intensity | Spacing 'd' | Relative intensity | Spacing 'd' | Relative intensity |
| 2.2290 | 3.0 | 2.4140 | 12.7 | 2.3446 | 8.4 |
| 2.1672 | 3.5 | 2.3567 | 8.5 | 2.3084 | 5.2 |
| 2.1125 | 3.4 | 2.3093 | 5.5 | 2.2682 | 4.1 |
| 2.0361 | 2.0 | 2.2801 | 6.1 | 2.2075 | 3.0 |
| 1.9911 | 3.3 | 2.1687 | 6.7 | 2.1667 | 4.1 |
| 1.9714 | 3.4 | 2.1303 | 4.5 | 2.0297 | 13.7 |
| 1.8935 | 2.5 | 2.0332 | 5.0 | 2.0023 | 3.5 |
| 1.8420 | 2.3 | 2.0031 | 6.6 | 1.8765 | 2.2 |
| 1.7917 | 2.0 | 1.9801 | 3.7 | 1.8019 | 2.6 |
| 1.7630 | 1.3 | 1.9395 | 2.7 | 1.4337 | 2.2 |
| 1.6723 | 1.1 | 1.8918 | 4.2 | 1.4005 | 0.4 |
| 1.5928 | 0.4 | 1.8632 | 3.5 | | |
| 1.4683 | 0.5 | 1.8354 | 3.0 | | |
| | | 1.8110 | 2.4 | | |
| | | 1.7812 | 2.1 | | |
| | | 1.7024 | 1.1 | | |
| | | 1.5414 | 0.6 | | |
| | | 1.3867 | 0.4 | | |

All the X-ray diffraction analysis were carried out by the powder diffraction method ($\lambda$=1.54060), the preparations of the sample were performed on a dry standard.

Diffractometer type: PW1710 BASED
Material of the anode: Copper.
Wavelength alpha1 [$\lambda$] = 1.54060   Wavelength alpha 2 [$\lambda$]: 1.54439
Initial angle [2θ°]: 5.010   Final angle[2θ°]; 69.810
Intensity ratio (alpha2/alpha1): 0.500
Maximum intensity: 3893.760

The X-ray (powder) diffraction pattern of the crystalline nitromethane, nitroethane and nitropropane solvates are reproduced in FIG. Ia, Ib and Ic respectively.

The I.R. spectra of the crystalline nitromethane, nitroethane and nitropropane solvates are reproduced in FIG. IIa, IIb and IIc respectively.

Subsequent drying of the crystalline solvate at 40° C./5-10 mmHg/60-70 hours, desolvates the crystalline compound to give amorphous quinapril hydrochloride of high purity which conforms to pharmacopoeial specifications. The crystalline solvate is typically dried at 40° C. under vacuum at 5-10 mmHg for 60-70 hours.

The quinapril thus obtained after drying is substantially free from impurities, specially the diketopiperazine compound of formula (II) and easily conforms to pharmacopoeial specifications and highly suitable for human use.

The invention can be further illustrated by the following examples, which, however, should not be construed as limiting the scope of the invention.

EXAMPLE-1

Preparation of the benzyl ester of (S,S,S)-2-[2-{(1-ethoycarbonyl)-3-phenylpropyl)amino]-1-oxopropyl]-1,2,3,4-tetrahydro-3-isoquinoline carboxylic acid; maleic acid salt (Quinapril benzyl ester maleic acid salt). (Method-I)

23 gms (0.089 moles) of N[1(S)-carboethoxy-3-phenylpropyl]-(S)-alanine (III) was taken in hexane, cooled to −5°

C. To this was added 20.5 gms of phosphorous pentachloride in lots, followed by purging of hydrogen chloride gas. The reaction mixture was stirred at 5-10° C. for 3 hrs. The acid chloride, which precipitated out, was filtered and washed with n-hexane.

35.4 gms (0.086 moles) of the para-toluene sulfonate salt of the benzyl ester of (S)-1,2,3,4-tetrahydro-isoquinoline-3-carboxylic acid (IV) was dissolved in 150 ml dichloromethane. 29 ms (0.287 moles) of triethyl amine was added at 0-5° C. and the reaction mixture stirred at 0-5° C. for 10 minutes. A solution of the acid chloride of compound (III) prepared in the earlier step in 150 ml of dichloromethane was added at −15 to −20° C. to the reaction mixture. The reaction mixture was then stirred at 20-25° C. for 1 hour. The organic phase was separated and washed with 200 ml of hydrochloric acid followed by 200 ml of water. The organic phase was then concentrated under vacuum. The residue of the quinapril benzyl ester was dissolved in 13 ml ethyl acetate and washed with 200 ml of 10% aqueous sodium bicarbonate solution followed by water wash (200 ml).

A solution of 9.4 gms of maleic acid dissolved in ethyl acetate was added to the organic phase containing quinapril benzyl ester. The reaction mixture was stirred at 25-30° C. for 30 minutes and filtered to afford 40 gms (70%) of the maleate salt (V); HPLC purity: >97%; m.p, 139.1° C.

$^1$H NMR (CDCl$_3$, 200 mHz) δ ppm: 7.0-7.40(m, 14.4), 6.30 (s, 2H), 5.45 (dd,2H), 5.05 (s, 2H), 4.7 (m, 2H), 4.4( m, 2H), 3.7 (m,1H), 3.05-3.45 (m,3H), 2.7-2.9 (m, 2H), 2.15-2.35 (m, 2H), 1.4-1.7(m, 3H), 1.3 (t, 3H)

I.R (KBr)(v, cm$^{-1}$): 3008, 1745, 1653, 1496, 1452, 1344, 1190, 1169, 1009, 984, 757, 652, 564.

EXAMPLE-2

Preparation of the benzyl ester of (S,S,S)-2-[2-{(1-ethoxycarbonyl)-3-phenylpropyl)amino]-1-oxopropyl]-1,2,3,4-tetrahydro-3-isoquinoline carboxylic acid; maleic acid salt. (Quinapril benzyl ester maleic acid salt). (Method-II)

50.0 gms (0.114 moles) of the para-toluene sulfonate salt of the benzyl ester of (S)-1,2,3,4tetrahydro-isoquinoline-3-carboxylic acid (IV) was added to a mixture of dichloromethane (150 ml) and water (150 ml). The mixture was cooled to 5° C., and the pH of the mixture was adjusted to 8.5 by dropwise addition of 25% aqueous ammonia (10 ml), at the same temperature, and stirred at 30° C. for 30 minutes. The organic layer containing the free base of (IV) was separated.

(43.4 gms; 0.142 moles) N[1(S)-carboethoxy-3-phenylpropyl]-(S)-alanyl carboxyanhydride (VI) was dissolved in dichloromethane (175 ml) at 30° C. The organic layer containing the free base of (IV) was added in 3.0 minutes at 30° C. The reaction mixture was monitored was stirred for 4.0 hours for the reaction to go to completion Triethyl amine (5.75 gms), followed by 10% sodium carbonate solution (100 ml) were added to the reaction mixture at 30° C., and stirred for 4.0 hours. The organic layer was separated and concentrated at 40° C. The residue was diluted with ethyl acetate (300 ml) and stirred to dissolve the residue at 40° C.

Maleic acid (13.21 gms) dissolved in ethyl acetate (350 ml) was added at 40° C. to the ethyl acetate layer containing the quinapril benzyl ester. The reaction mixture was stirred for 30 minutes at 30° C. and then cooled to 0° C. The mixture was stirred for 30 minutes and filtered. The wet cake was washed with ethyl acetate and dried at 50° C./10-20 mmHg for 6.0 hours, to afford 55.74 gms (76%) of the maleate salt (V); HPLC purity: >98%; m.p, 139.1° C.

1H NMR (CDCl$_3$, 200 mHz) δ ppm: 7.0-7.40(m, 14.4), 6.30 (s, 2H), 5.45 (dd,2H), 5.05 (s, 2H), 4.7 (m, 2H), 4.4(m, 2H) 3.7 (m,1H), 3.05-3.45 (m,3H) 2.7-2.9 (m, 2H), 2.5-2.35 (m, 2H), 1.4-1.7(m, 3H), 1.3 (t, 3H)

I.R. (KBr)(v, cm$^{-1}$): 3008, 1745, 1653, 1496, 1452, 1344, 1190, 1169, 1009, 984, 757, 652, 564.

EXAMPLE-3

Preparation of (S,S,S)2-{2-[(1-ethoxycarbonyl-3-phenylpropyl)amino]-1-oxopropyl]-1,2,3,4-tetrahydroisoquinoline-3-carboxylic acid hydrochloride. (Quinapril hydrochloride)

The conversion of quinapril benzyl ester maleic acid salt (V) as obtained in examples (1 & 2) to quinapril hydrochloride (I) is achieved by the following steps:

A. Formation of Quinapril Benzyl Ester Free Base.

25 gms (0.0388 moles) quinapril benzyl ester maleic acid salt (V) obtained in Example-1 was dissolved in a mixture of 125 ml water and 125 ml dichloromethane. The pH of the solution was adjusted between 7.5 to 8.5 by addition of aqueous ammonia. Reaction mixture was stirred for 30 minutes, the organic phase separated and washed with 50 ml water. The organic phase was separated and treated with activated carbon. After filtration, the organic phase was evaporated under reduced pressure below 40° C., the free base of quinapril benzyl ester was obtained.

B. Debenzylation of Quinapril Benzyl Ester (Preparation of Quinapril Hydrochloride).

The benzyl ester free base obtained in Step A is dissolved in 140 ml ethanol to which 1.0 gm of 10% Pd/C and 6.0 gms of 35% hydrochloric acid are added. The reaction mass is subjected to catalytic hydrogenolysis with hydrogen gas at 40-60 psi pressure and 20-30° C. The reaction mass is filtered and the filtrate evaporated to give crude quinapril hydrochloride. The residue is dissolved in dichloromethane and the solvent recovered below 35° C. under reduced pressure: This operation is repeated till the water content of the residue is less than 1.0%.

EXAMPLE-4

Crystallisation of quinapril hydrochloride (I) form Nitromethane

Nitromethane (125 ml) is added to the anhydrous residue of quinapril hydrochloride obtained in Step B, Example-3 and the mixture is stirred at 20-25° C. for 10-15 minutes to get a clear solution. The mixture is stirred at the same temperature for 30 minutes and seeded with pure quinapril hydrochloride. The mass is cooled to 5-10° C., and stirred at the same temperature for 2 hrs. The reaction mass is then filtered at 20-25° C. and the wet cake is washed with nitromethane. (50 ml) to give crystalline quinapril hydrochloride associated with a solvate of nitromethane, having HPLC Purity >99% and X-ray (powder0 diffraction pattern as summarized in Table-I and FIG.-Ia.

IR (KBr) (v,cm$^{-1}$): 3030, 2933, 2856, 2796, 1743, 1701, 1645, 1550, 1490, 1450, 1263, 1197, 1091, 756, 729, 707.

Solid state $^{13}$C CPMAS at 10 KHz: 255.04, 221.26, 212.38 207.50 175.6, 168.7, 141.9, 132.93, 127.16, 96.07, 89.25, 87.34, 62.79, 60.01, 56.71, 53.41, 47.63, 35.76, 14.58.

| DSC (50.0-300.0° C.; 05.00° C./min): | Integral: −233.25 mJ<br>Onset: 96.99° C.<br>Peak: 107.39° C.<br>Endset: 111.55 | Integral: −245.18 mJ<br>Onset: 151.25° C.<br>Peak: 163.53° C.<br>Endset: 172.43° C. |
|---|---|---|

The crystalline nitromethane solvate is then dried at 40° C./0-5 mm Hg pressure for 60 hours to give pure amorphous quinapril hydrochloride; m. p. 117-121° C.; $[\alpha]_d$ (2% in $CH_3OH$): +14.92 in a yield of 65%.

$^1$HNMR: ($CDCl_3$, 200 mHz) δ ppm: 10.0(bs, 1H), 8.9(bs, 1H), 7.08 (m, 9H), 5.05 (m, 1H), 4.35-4.95(m, 3H), 3.7-4.3 (m, 3H), 2.9-3.4(, 2H), 2.45-2.85(m, 2H), 2.1-2.4(m, 2H), 1.4-1.8(dd, 3H), 1.0-1.25(m, 3H).

IR (KBr)(v, cm$^{-1}$): 2981, 2858, 1739, 1649, 1535, 1496 1438, 1369, 1259, 1207, 750, 702.

EXAMPLE-5

Crystallisation of quinapril hydrochloride from nitroethane

Nitroethane (125 ml) is added to the anhydrous residue of impure quinapril hydrochloride obtained in step B, Example-3 and the mixture is stirred at 20-25° C. for 10-15 minutes to get a clear solution. The mixture is stirred at the same temperature for 30 minutes and seeded with pure quinapril hydrochloride. The mass is cooled to 5-10° C., and stirred at the same temperature for 2 hrs. The reaction mass is then filtered at 20-25° C. and the wet cake is washed with nitroethane (50 ml) to give crystalline quinapril hydrochloride associated with a solvate of nitroethane, having HPLC purity >99% and X-ray (powder) diffraction pattern as summarized in Table-I and FIG-Ib.

IR (KBr) (v,cm$^{-1}$): 3435, 2849, 1742, 1707, 1642, 1553, 1492, 1450, 1430, 1408, 1368, 1298, 1261, 1195, 1040, 757.

| DSC (50.0-300.0° C.; 05.00° C./min): | Integral: −716.23 mJ<br>Onset: 97.32° C.<br>Peak: 106.64° C.<br>Endset: 111.39 | Integral: −357.15 mJ<br>Onset: 157.48° C.<br>Peak: 164.09° C.<br>Endset: 170.80° C. |
|---|---|---|

The crystalline nitroethane solvate is then dried at 40° C. /0-5 mm Hg pressure for 60 hours to give pure amorphous quinapril hydrochloride, m. p 117-121° C.; $[\alpha]_d$ (2% in $CH_3OH$): +14.92 in a yield of 65%.

$^1$HNMR: ($CDCl_3$, 200 mHz) δ ppm: 10.0(bs, 1H), 8.9(bs, 1H), 7.08 (m, 9H), 5.05 (m, 1H), 4.35-4.95(m,3H), 3.7-4.3 (m,3H), 2.9-3.4(,2H), 2.45-2.85(m, 2H), 2.1-2.4(m, 2H), 1.4-1.8(dd, 3H), 1.0-1.25(m, 3H).

IR (KBr)(v, cm$^{-1}$): 2981, 2858, 1739, 1649, 1535, 1496, 1438, 1369, 1259, 1207, 750, 702.

EXAMPLE-6

Crystallisation of quinapril hydrochloride from nitropropane

Nitropropane (125 ml) is added to the anhydrous residue of quinapril hydrochloride from step B, Example-3 and the mixture is stirred at 20-25° C. for 10-15 minutes to get a clear solution. The mixture is stirred at the same temperature for 30 minutes and seeded with pure quinapril hydrochloride. The mass is cooled to 5-10° C., and stirred at the same temperature for 2 hrs. The reaction mass is then filtered at 20-25° C. and the wet cake is washed with nitropropane (50 ml) to give and crystalline quinapril hydrochloride associated with a solvate of nitropropane, having HPLC purity >99% and X-ray (powder) as summarized in Table-I and FIG.-Ic.

IR (KBr) (v, cm$^{-1}$): 3420, 2850, 1742, 1705, 1643, 1547, 1495, 1451, 1437, 1408, 1334, 1296, 1259, 1225, 1091, 1041, 757, 497.

| DSC (50.0-300.0° C.; 05.00° C./min): | Integral: −325.52 mJ<br>Onset: 92.34° C.<br>Peak: 95.15° C.<br>Endset: 97.17° C. | Integral: −419.74 mJ<br>Onset: 152.58° C.<br>Peak: 159.63° C.<br>Endset: 173.72° C. |
|---|---|---|

The crystalline material is then dried at 40° C./0-5 mm Hg pressure for 60 hours to give amorphous quinapril hydrochloride, m. p. 117-121° C.; $[\alpha]_d$ (2% in $CH_3OH$): +14.92 in a yield of 65%.

$^1$H NMR:($CDCl_3$, 200 ppm) δ ppm: 10.0(bs, 1H), 8.9(bs, 1H), 7.08 (m, 9H), 5.05 (m,1H), 4.35-4.95(m, 3H), 3.7-4.3 (m, 3H), 2.9-3.4(,2H), 2.45-2.85(m, 2H), 2.1-2.4(m, 2H), 1.4-1.8(dd, 3H), 1.0-1.25(m, 3H).

IR (KBr)(v, cm$^{-1}$): 2981, 2858, 1739, 1649, 1535, 1496, 1438, 1369, 1259, 1207, 750, 702.

The invention claimed is:

1. A crystalline nitroalkane solvate of quinapril hydrochloride of formula (I)

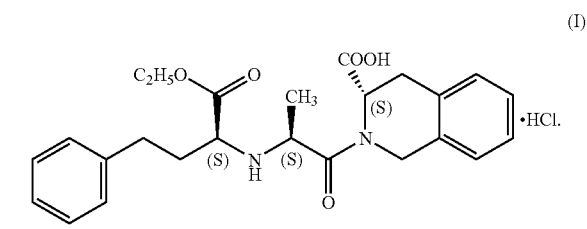

2. The crystalline nitroalkane solvate quinapril hydrochloride as claimed in claim 1 wherein the nitroalkane is nitromethane, said nitromethane solvate of quinapril hydrochloride exhibiting essentially the following X-ray (powder) diffraction data:

| Spacing 'd' | Relative intensity |
|---|---|
| 16.2471 | 63.5 |
| 13.8426 | 55.5 |
| 11.9609 | 57.3 |
| 9.6467 | 17.2 |
| 7.9468 | 22.4 |
| 7.5064 | 31.1 |
| 7.1699 | 30.2 |
| 6.4095 | 52.4 |
| 6.0561 | 3.1 |
| 5.5041 | 20.4 |
| 5.2808 | 33.1 |
| 5.1767 | 22.8 |
| 4.8704 | 5.7 |
| 4.6830 | 34.4 |
| 4.4404 | 100 |
| 4.0977 | 30.9 |
| 3.9931 | 69.5 |
| 3.7747 | 62.8 |
| 3.5972 | 12.9 |
| 3.5058 | 22.8 |

-continued

| Spacing 'd' | Relative intensity |
|---|---|
| 3.4153 | 8.3 |
| 3.3558 | 7.0 |
| 3.2676 | 30.7 |
| 3.2054 | 7.6 |
| 3.1510 | 9.5 |
| 3.0854 | 16.5 |
| 2.9772 | 14.5 |
| 2.9403 | 17.5 |
| 2.9122 | 12.9 |
| 2.7798 | 7.6 |
| 2.6670 | 9.0 |
| 2.6216 | 6.0 |
| 2.5613 | 10.1 |
| 2.4650 | 5.2 |
| 2.3933 | 7.9 |
| 2.2963 | 4.9 |
| 2.2620 | 2.7 |
| 2.2290 | 3.0 |
| 2.1672 | 3.5 |
| 2.1125 | 3.4 |
| 2.0361 | 2.0 |
| 1.9911 | 3.3 |
| 1.9714 | 3.4 |
| 1.8935 | 2.5 |
| 1.8420 | 2.3 |
| 1.7917 | 2.0 |
| 1.7630 | 1.3 |
| 1.6723 | 1.1 |
| 1.5928 | 0.4 |
| 1.4683 | 0.5. |

3. The crystalline nitroalkane salvate quinapril hydrochloride as claimed in claim 1 wherein the nitroalkane is nitroethane, said nitroethane solvate of quinapril hydrochloride exhibiting essentially the following X-ray (powder) diffraction data:

| Spacing 'd' | Relative intensity |
|---|---|
| 17.4844 | 87.0 |
| 16.0841 | 67.2 |
| 12.0996 | 53.3 |
| 10.0860 | 18.8 |
| 8.1700 | 29.6 |
| 7.7522 | 41.2 |
| 7.3814 | 35.4 |
| 6.5032 | 39.9 |
| 6.0580 | 2.9 |
| 5.5780 | 35.8 |
| 5.3973 | 32.0 |
| 5.2776 | 23.7 |
| 4.9335 | 19.6 |
| 4.8335 | 32.9 |
| 4.7627 | 40.5 |
| 4.5635 | 88.9 |
| 4.5095 | 69.6 |
| 4.4227 | 36.5 |
| 4.2021 | 36.0 |
| 4.0818 | 100.0 |
| 3.8719 | 30.4 |
| 3.7802 | 48.7 |
| 3.6435 | 49.5 |
| 3.4889 | 10.4 |
| 3.3520 | 20.8 |
| 3.2948 | 36.3 |
| 3.1526 | 15.3 |
| 3.1132 | 19.1 |
| 3.0304 | 49.5 |
| 2.9280 | 19.2 |
| 2.9080 | 14.1 |
| 2.7933 | 7.9 |
| 2.6986 | 10.8 |

-continued

| Spacing 'd' | Relative intensity |
|---|---|
| 2.6399 | 9.4 |
| 2.5715 | 16.7 |
| 2.5194 | 9.6 |
| 2.4535 | 4.6 |
| 2.4140 | 12.7 |
| 2.3567 | 8.5 |
| 2.3093 | 5.5 |
| 2.2801 | 6.1 |
| 2.1687 | 6.7 |
| 2.1303 | 4.5 |
| 2.0332 | 5.0 |
| 2.0031 | 6.6 |
| 1.9801 | 3.7 |
| 1.9395 | 2.7 |
| 1.8918 | 4.2 |
| 1.8632 | 3.5 |
| 1.8354 | 3.0 |
| 1.8110 | 2.4 |
| 1.7812 | 2.1 |
| 1.7024 | 1.1 |
| 1.5414 | 0.6 |
| 1.3867 | 0.4. |

4. The crystalline nitroalkane solvate quinapril hydrochloride as claimed in claim 1 wherein the nitroalkane is nitropropane, said nitropropane solvate of quinapril hydrochloride exhibiting essentially the following X-ray (powder) diffraction data:

| Spacing 'd' | Relative intensities |
|---|---|
| 17.4327 | 100.0 |
| 15.4378 | 65.5 |
| 12.1079 | 49.5 |
| 10.4492 | 18.2 |
| 8.3626 | 21.3 |
| 7.9183 | 38.9 |
| 7.5253 | 27.5 |
| 6.6268 | 19.6 |
| 6.4583 | 17.2 |
| 5.6238 | 43.2 |
| 5.2713 | 27.8 |
| 5.1011 | 18.3 |
| 4.9816 | 30.7 |
| 4.8049 | 38.7 |
| 4.6878 | 52.0 |
| 4.5427 | 61.4 |
| 4.4480 | 35.3 |
| 4.3008 | 25.3 |
| 4.1690 | 68.6 |
| 4.0279 | 14.7 |
| 3.9483 | 23.9 |
| 3.7993 | 57.5 |
| 3.5871 | 15.5 |
| 3.4582 | 14.8 |
| 3.2960 | 32.0 |
| 3.1558 | 20.6 |
| 3.1053 | 26.1 |
| 3.0548 | 17.9 |
| 2.9559 | 9.2 |
| 2.9066 | 9.9 |
| 2.8044 | 10.6 |
| 2.7274 | 6.5 |
| 2.6357 | 9.4 |
| 2.5910 | 11.1 |
| 2.4880 | 5.3 |
| 2.4365 | 6.4 |
| 2.4053 | 6.0 |
| 2.3446 | 8.4 |
| 2.3084 | 5.2 |
| 2.2682 | 4.1 |
| 2.2075 | 3.0 |

-continued

| Spacing 'd' | Relative intensities |
| --- | --- |
| 2.1667 | 4.1 |
| 2.0297 | 13.7 |
| 2.0023 | 3.5 |
| 1.8765 | 2.2 |
| 1.8019 | 2.6 |
| 1.4337 | 2.2 |
| 1.4005 | 0.4. |

5. A process for preparation of quinapril hydrochloride of formula (I)

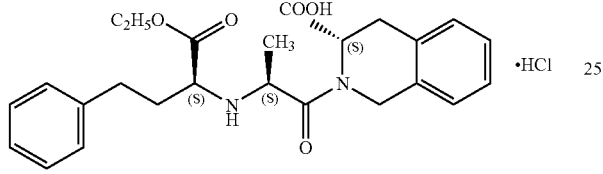
(I)

which comprises the steps of:
a) adjusting the pH between 7.5-8.5 of a solution of the benzyl ester maleate salt of quinapril of formula (V) in a mixture of water and an organic solvent to obtain free base compound of formula (V),

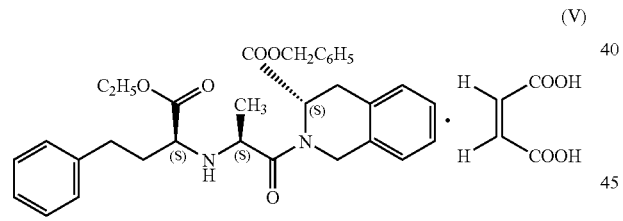
(V)

b) subjecting the free base of compound (V) thus obtained in step a) to catalytic hydrogenation in an alcoholic solvent in the presence of concentrated hydrochloric acid or hydrogen chloride dissolved in an alcoholic solvent and in the presence of catalytic amounts of Pd/C to obtain a residue containing formula (I),
c) crystallization of the residue containing compound of formula (I) thus obtained by evaporating the alcoholic solvent from step b) from a nitroalkane solvent to give crystalline quinapril hydrochloride, associated with a solvate of the nitroalkane solvent, and
d) drying the crystalline quinapril hydrochloride nitroalkane solvate obtained in step c) at a temperature between 40° C. and 45° C. under vacuum to give pure quinapril hydrochloride of formula (I).

6. The process according to claim 5, wherein the benzyl ester maleate salt of quinapril of formula (V),

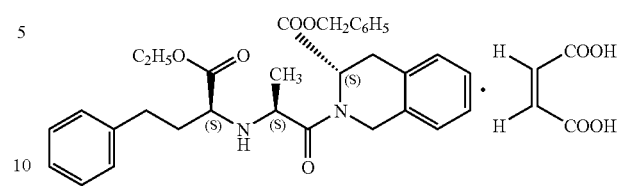
(V)

is obtained by reacting the acid halide of compound of formula (III).

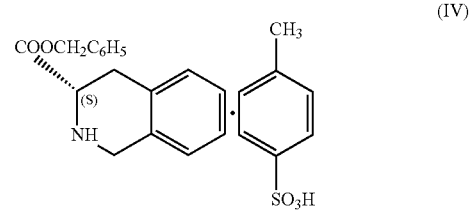
(III)

with, compound of formula (IV)

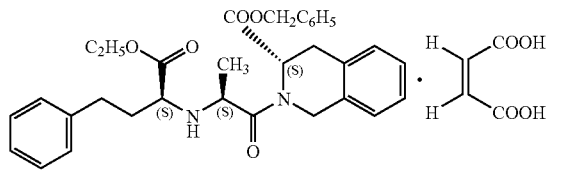
(IV)

in an organic solvent and in the presence of a base followed by addition of maleic acid.

7. The process according to claim 5, wherein the benzyl ester maleate salt of quinapril of formula (V),

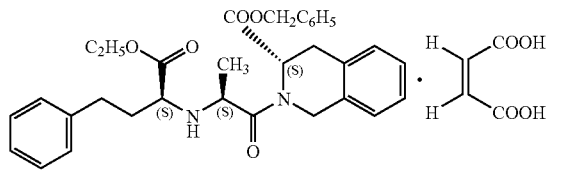
(V)

is obtained by reacting the compound of formula (VI),

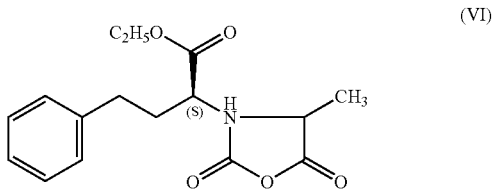
(VI)

with a compound of formula (IV),

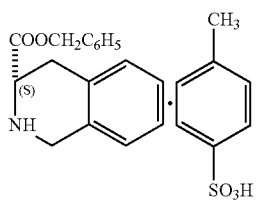

in an organic solvent and in the presence of a base followed by addition of maleic acid.

8. The process according to step (a) of claim 5, wherein the organic solvent is selected from a chlorinated hydrocarbon.

9. The process according to claim 8, wherein the chlorinated hydrocarbon is selected from dichloromethane, 1,2-dichloroethane and chloroform.

10. The process according to step (a) of claim 5, wherein the pH is adjusted using aqueous ammonia.

11. The process according to step (b) of claim 5, wherein the alcoholic solvent is selected from methanol, ethanol, n-propanol and isopropanol.

12. The process according to step (c) of claim 5, wherein the nitroalkane solvent is selected from nitromethane, nitroethane and nitropropane.

13. The process according to step (c) of claim 5, wherein the compound obtained in Step (b) is dissolved in the nitroalkane solvent at room temperature.

14. The process according to step (c) of claim 5, wherein the crystallization is carried out a temperature ranging from −15° C. to +15° C.

15. The process according to claim 14, wherein the crystallization is carried out a temperature ranging from 0° C. to 10° C.

16. The process according to step (d) of claim 5, wherein the drying is carried out under a vacuum of 5-10 mm Hg and lasts from about 60 to about 70 hours.

17. The process according to claim 6, wherein the acid halide is acid chloride or acid bromide.

18. The process according to claim 6, wherein The organic solvent is selected from a chlorinated hydrocarbon or an alkyl acetate.

19. The process according to claim 18, wherein the chlorinated hydrocarbon is selected from dichloromethane, 1,2-dichloroethane and chloroform.

20. The process according to claim 18, wherein the alkyl acetate is selected from methyl acetate, ethyl acetate and butyl acetate.

21. The process according to claim 6, wherein the base is an organic base.

22. The process according to claim 21, wherein the organic base is selected from triethylamine, diethylamine, tertiary butylamine, and dicyclohexylamine.

23. The process according to claim 7, wherein the organic solvent is selected from a chlorinated hydrocarbon or an alkyl acetate.

24. The process according to claim 23, wherein the chlorinated hydrocarbon is selected from dichloromethane, 1,2-dichloroethane and chloroform.

25. The process according to claim 23, wherein the alkyl acetate is selected from methyl acetate, ethyl acetate and butyl acetate.

26. The process according to claim 7, wherein the base is an organic base.

27. The process according to claim 7, wherein the base is an inorganic base.

28. The process according to claim 26, wherein the organic base is selected from triethylamine, diethylamine, tertiary butylamine, and dicyclohexylamine.

29. The process according to claim 27, wherein the inorganic base is selected from sodium carbonate, sodium bicarbonate, potassium carbonate, potassium bicarbonate.

* * * * *